United States Patent [19]

Schelhas

[11] Patent Number: 4,856,503
[45] Date of Patent: Aug. 15, 1989

[54] DEVICE FOR CUTTING A THREAD IN A CUP-SHAPED BONE

[75] Inventor: Klaus-Dieter Schelhas, Bremen, Fed. Rep. of Germany

[73] Assignee: Orthoplant Endoprothetik GmbH, Bremen, Fed. Rep. of Germany

[21] Appl. No.: 192,211

[22] Filed: May 10, 1988

[30] Foreign Application Priority Data

Aug. 15, 1987 [DE] Fed. Rep. of Germany ... 8711113[U]

[51] Int. Cl.⁴ ............................................. A61B 17/16
[52] U.S. Cl. .............................. 128/92 VJ; 128/92 V; 128/305; 408/80; 408/81
[58] Field of Search ........... 128/92 V, 92 VJ, 92 VY, 128/92 VV; 623/22, 23; 10/140, 141 R; 408/74, 79, 80, 81

[56] References Cited

U.S. PATENT DOCUMENTS 3,412,733 11/1968 Ross ..................... 128/92 VJ X
4,131,116 12/1978 Hedrick ....................... 128/305
4,271,849 6/1981 Rehder ..................... 128/92 VD X
4,611,587 9/1986 Powlan ..................... 128/982 VJ
4,662,891 5/1987 Noiles ..................... 128/92 VJ X

FOREIGN PATENT DOCUMENTS 147339 7/1985 European Pat. Off. ........ 128/92 VJ
2457713 6/1976 Fed. Rep. of Germany ... 128/92 VJ
2834296 2/1980 Fed. Rep. of Germany .

Primary Examiner—Robert A. Hafer
Assistant Examiner—Kevin G. Rooney
Attorney, Agent, or Firm—Merchant, Gould, Smith, Edell, Welter & Schmidt

[57] ABSTRACT

Given is a device for cutting a thread in a cup-shaped bone, in particular in the acetabulum of a human pelvis bone, which includes a cutter holder on a drive shaft, with a radially, outwardly directed cutting blade being disposed on the cutter holder. In order to cut, in simple fashion, a correctly dimensioned threading into the bone tissue with a desired depth of cut, the device includes a cutter gauge capable of being fixed in the cup space, with the cutter gauge having a central boring and an open cutting channel running spirally about the longitudinal axis of the boring. The cutter holder is capable of being introduced centrally into the boring of the cutter gauge and is capable of being set into a forcefully guided, spiral cutting movement with introduction of the blade into the cutting channel, during the course of which the cutting blade cuts the thread precisely in the bone tissue.

18 Claims, 2 Drawing Sheets

DEVICE FOR CUTTING A THREAD IN A CUP-SHAPED BONE

TECHNICAL FIELD

The invention concerns a device for cutting a thread in a cup-shaped bone, in particular in the acetabulum of a human pelvis bone, with a cutter holder on a drive shaft and with a radially, outwardly directed cutting blade on the cutter holder.

BACKGROUND OF THE INVENTION

Known from DE-OS 28 34 296 is a device of this kind where the cutter holder displays a hemispherical shape filling the hollow cup space and a radially extendable cutting blade that serves for cutting relieved grooves in the acetabular tissue of the human pelvis bone. However, since the bone tissue of the human acetabulum has a different hardness in different parts of the surface and, in particular, is highly sclerosed in the support zone of the femur head, the cutting blade preferably penetrates into the bone tissue in the soft superficial areas; on the other hand, the particularly hard bone tissue will urge the cutting blade out from the bone and, therewith, also bring the cutter holder into an erroneous position in the acetabulum, so that the cut generated in the bone tissue runs unequally deep in different superficial areas and, overall, does not come to desired dimensions very well.

Moreover, there are thread cutters for cutting threads in the acetabulum of the human pelvis bone that likewise have a round body, with a cutting thread revolving externally, approximately filling the acetabulum. Because of the different hardness of the surface of the acetabulum, these thread cutters also slip out of their desired central working position such that the cutting thread penetrates essentially only into the soft regions of the bone tissue, on the other hand can not penetrate into the hard surface regions. Hence, obtained as a result is a thread that runs too deeply in the soft superficial zones and not deeply enough into the bone tissue in the hard superficial zones. Next, if an artificial hip cup is screwed with its external threading into a thread of this type, an adequate bond between hip cup and bone occurs only in the soft bone tissue; the desired, firm anchoring bond between artificial hip cup and the bone tissue is not achieved, in particular in the hard bone tissue.

SUMMARY OF THE INVENTION

In comparison to this, the object of the invention is to develop further a device of the initially mentioned kind such that, in a simple manner, it is possible to cut an exactly dimensioned thread into the bone tissue having throughout the desired depth of cut.

In the case of the device of the initially mentioned kind, this objective is met in accordance with the invention by the fact that there is provided, in the cup space, a fastenable cutter gauge with a central boring and an open cutting channel running spirally about the longitudinal axis of the boring, and that the cutter holder can be introduced centrally into the boring of the cutter gauge and is capable of being set into a forcefully guided sprial cutting movement with introduction of the cutting blade into the cutting channel.

The advantages of the invention lie in particular in the fact that fixed in the acetabulum is a cutter gauge filling the hollow cup space and that, next, cut with a cutting tool, consisting of a cutter holder and of a cutter gauge, is a thread, with the cutting blade being forcefully guided in the radially open cutting channel of the cutter gauge and, when driving the cutting tool, executes the forcefully guided, spiral cutting movement. Since the cutter gauge is firmly held undisplaceably by hand in the acetabulum, mechanically or by auxiliary holding arrangements, runout or dislodging of the cutting blade in the bone areas of different hardness is not possible. More to the point, the cutting blade will run along the forced path prescribed exactly by the cutting channel and thereby generate a correctly dimensioned thread having the set cut depth, in particular, during a cutting procedure, the cutter holder is guided in the central boring of the cutter gauge with little play, so that it can execute exactly centrically the screwing movement prescribed by the cutting blade.

In particularly preferred fashion, the cutting blade is journaled in radially displaceable fashion in the cutter holder, and the radial position of the cutting blade can be adjusted and fixed with setting elements. With a device of this type it is then also possible to produce exactly threads with particularly great cut depths, in several sequential cutting procedures, with the cutting blade being adjusted and fixed further radially outward for each subsequent cutting procedure, so that the final cut depth is achieved in steps without changing the cutting tool. This form of embodiment of the invention is particularly advantageous when cutting in the acetabulum the required threading for emplacing artificial hip cups, because, in particular, the zones with hard bone tissue do not permit cutting thread courses having the desired, final cup depth in a single step.

In particularly preferred fashion, the cutter gauge has a hemispherical external form adapted to the hollow socket space of the acetabulum, and having on the external surface fixing pins directed outwardly against the bone. For fixing the cutter gauge, this latter is set into the acetabulum and then —e.g. with a light hammer blow —anchored in the bone with the fixing pins. Additionally, it is possible to install additionally on the cutter gauge attaching means, e.g. threaded boxes, etc., to which hand grips can be attached so that the cutter gauge can additionally be held by hand.

In particularly preferred fashion, the cutter holder, in a coaxial extension of the drive shaft, has a cylindrical form fitting into the boring of the cutter gauge. Provided externally on the cutter holder is an external threading running about its central axis, the pitch of which is the pitch of the cutting channel of the cutter gauge so that the external threading of the cutter holder is guided inside the cutting channel at the time of, or after, introduction into the cutter gauge and thereby effects an exact guidance of the cutter holder during the entire cutting movement.

Preferentially, the free end of the cutter holder is constructed hemispherically and, when starting up, serves as a stop against the floor of the hollow cup space, said stop preventing further cut-in of the cutter holder and thereby limiting the cutting procedure. Additionally, at least one other mechanical stop can be provided in the cutter gauge, against which the cutter holder or the cutting blade can run at the end of a cutting movement and thereby terminate the cutting procedure without damaging the pelvis bone.

The cutting blade is preferentially journaled in radially displaceable fashion in a radial groove at the hemispherically shaped end of the cutter holder and has, in the radial direction, a gearing that cooperates with a setting pinion journaled in the cutter holder. The setting pinion is preferentially coupled with an adjustment element with which the operator can adjust the position and, therewith, the depth of cut of the cutting blade. Preferentially provided as an adjusting element is a hollow shaft about the drive shaft which, with an external gearing, cooperates with the setting pinion in the cutter holder. The hollow shaft can be provided with a uniform gearing in order to enable easy production of the cutting blade. Present between the hollow shaft and the drive shaft are arresting means for releasable fixing of the radial position, said means preferentially including a circumferential gearing on the drive shaft or on the hollow shaft, and a spring loaded arresting element cooperating with the circumferential gearing.

In a particularly preferred manner, the device in accordance with the invention has means for feeding and leading away a rinsing solution at the cutting location. For this purpose, the drive shaft is preferentially constructed as a double-walled, coaxial hollow shaft that includes between the outer and the inner hollow shaft a ring chamber for inflow of the rinsing solution, e.g. common salt solution, and in the inner hollow shaft a channel for leading off the rinsing solution, with an inlet and outlet feed coupling being provided at a predetermined distance from the cutter holder, said coupling being joined through means of a ring channel with the circular inflow channel and, with another ring channel, joined with the outflow channel.

In a particularly preferred manner, capable of being attached to the drive shaft, e.g. by means of a chuck jaw, on the end of the drive shaft lying opposite to the cutter holder, is an actuating crank. The drive shaft and/or the inner hollow shaft of the drive shaft is capable of being firmly, or also releasably, joined with the cutter holder. The external hollow shaft of the drive shaft as well as the external hollow shaft serving as an adjusting means for the cutting blade can —like the setting pinion—and like the coupling be plugged on to the drive shaft and/or the inner hollow shaft of the drive shaft for feeding in and leading off the rinsing solution. Then the chuck jaw preferentially serves for the purpose of establishing the axial position of the plug-on parts of the device.

Advantageous further developments of the invention are characterized by the features of the subclaims.

BRIEF DESCRIPTION OF THE DRAWINGS

Described in further detail in the following with the aid of the drawing is an example of embodiment of the invention.

DETAILED DESCRIPTION OF THE INVENTION

Figure 1:
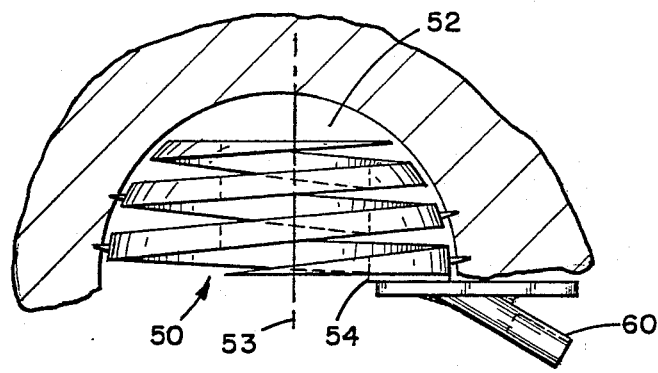
FIG. 1 shows a side view of the cutter gauge.

FIG. 1 shows a side view of a cutter gauge 50, which is a component part of the cutting device in accordance with the invention, emplaced in the acetabulum of the human pelvis bone.

Figure 2:
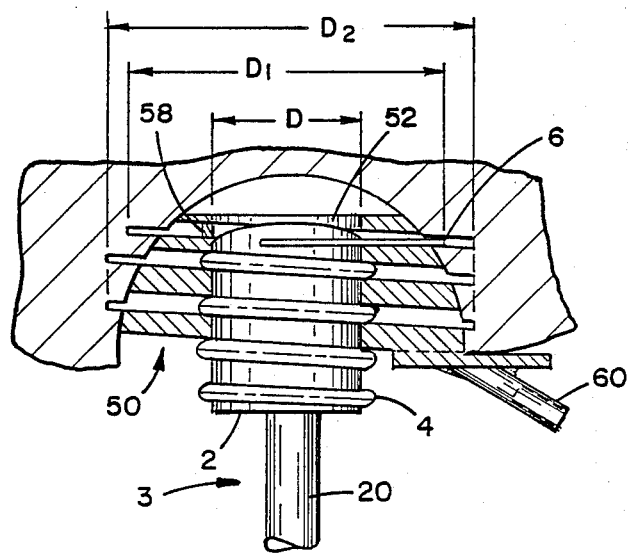
FIG. 2 shows a cut through the cutter gauge of FIG. 1 with introduced cutter holder.

FIG. 2 shows a cut through the cutter gauge 50 represented in FIG. 1, together with the cutting tool 3 emplaced in the cutter gauge 50. The cutter gauge 50 has a hemispherical external form adapted to the hollow cup space of the acetabulum and a central boring 52 with a comparatively large diameter. Running spirally about the longitudinal axis 53 of the boring 52 is an open cutting channel 54 that represents a spiral gap opening extending from the boring to the bone. The cutter gauge has outwardly directed, pointed fixing pins 56 on its external surface and a stop 58 at the top end of the cutting channel 54. Welded to the lower base surface 59 of the cutter gauge lying in the cup opening are attaching means 60 which, for example, have an internal threading for screwing on hand grips.

FIG. 2 shows a cross section through the cutter gauge 50 that is emplaced in the acetabulum. Represented besides this is the cutting tool 3 that includes a cutter holder 2, to which is centrally attached a drive shaft 20. The cutter holder has a cylindrical form fitting into the boring 52 of the cutter gauge 50 as well as an external threading running about its axis of symmetry, the pitch of the thread being equal to the pitch of the cutting channel 54. The free end of the cutter holder is convexly rounded and has a radially running guide groove 5 in which is journaled, radially directed and radially displaceable, a cutting blade 6, with the cutting blade 6 being disposed in the external threading and/or in extension of the screw line of the external thread 4, so that the part of the cutting blade 6 projecting out from the cutter holder 2 is also guided inside the cutting channel 54 when the external threading 4 is screwed into the cutting channel 54. Alternatively, it is also possible to do away with the external threading 4. The cutter holder 2 is then guided in the boring 52, while the cutting blade can execute its spiral, forcefully guided cutting movement inside the cutting channel when the drive shaft is set into a rotating movement.

Because of the particular hardness of the bone tissue surrounding the hollow cup space, the cutting procedure is carried out in several steps up to the final cut depth. Therefore, in FIG. 2, the cut thread is represented during a second cutting procedure that is carried out with a diameter of $D_2$. The upper part of the cut thread was cut in the preceding first cutting procedure having a diameter of $D_1$, further cutting procedures with large diameter and with the cutting blade 6 extended correspondingly further out can follow.

Figure 4:
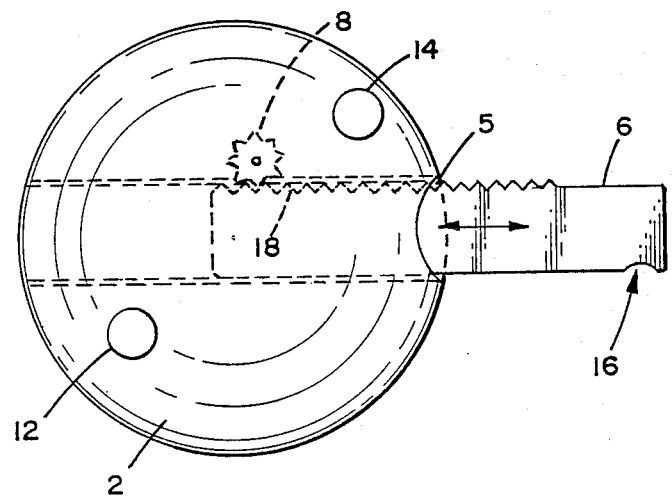
FIG. 4 shows a top view onto the cutter holder in accordance with FIG. 3.
Figure 3:
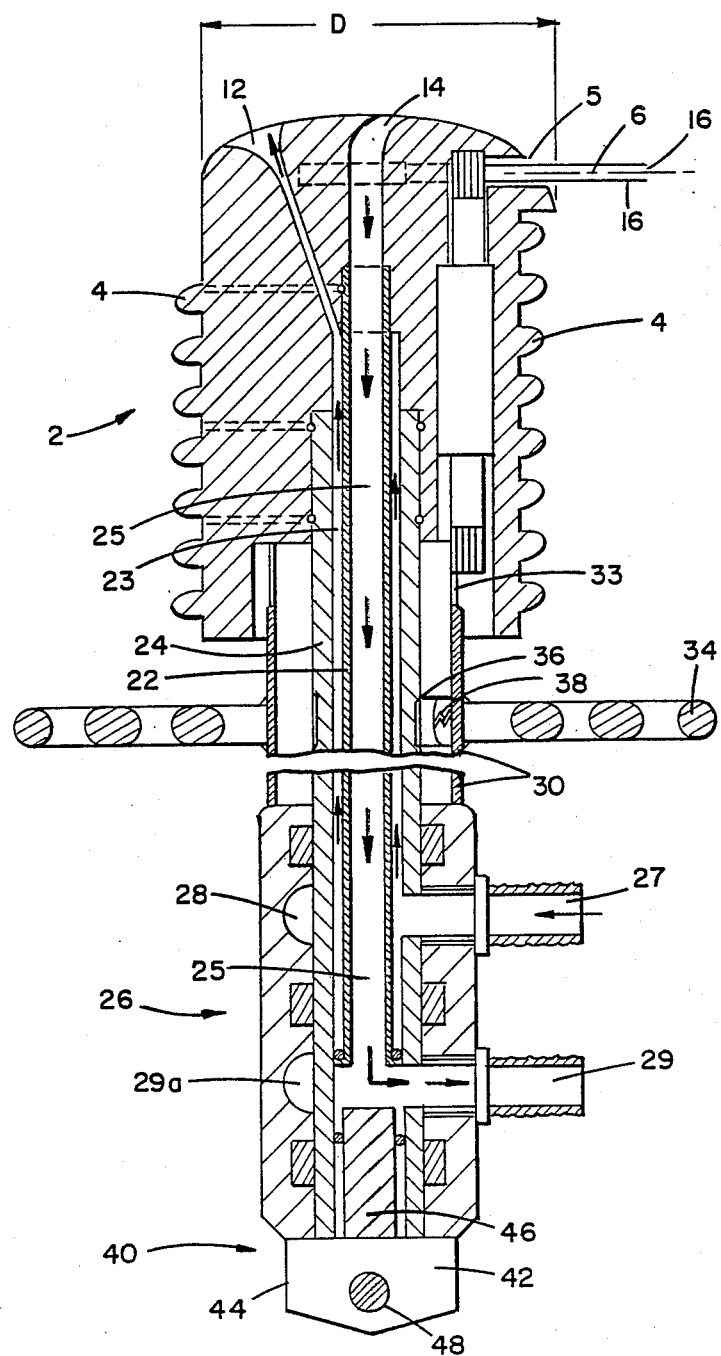
FIG. 3 shows a side view of the cutting tool, partially in a cut.

FIGS. 3 and 4 show a cut, respectively a top view onto the cutting tool 3. The cutter holder 2 has the form of a cylindrical body fitting into the boring 52 of the cutter gauge 50, with external threading 4 about the axis of symmetry of the cutter holder, the drive shaft 20 running in its extension and attached to the cutter holder. The cutter holder displays at its free end a radial guide groove 5 in which the cutting blade 6 is journaled in radially displaceable fashion, compare FIG. 4. The cutting blade 6 has, at least at its radially extendable end, a cutting edge 16; it additionally has, in the radial direction, a gearing 18 that cooperates with a setting pinion 8 that is rotatably journaled in the cutter holder 2, parallel to the axis of the drive shaft 20.

The drive shaft 20 has an inner hollow shaft 22 and spaced therefrom an external hollow shaft 24, both being joined in rotation-fast manner with the cutter holder 2. Another hollow shaft 30 is disposed about both hollow shafts 22, 24 of the drive shaft and serves as an adjusting element that cooperates, by means of an external gearing 33, with the setting pinion 9 that engages into the gearing 18 of the cutting blade 6 and radially adjusts the cutting blade. Attached to the hollow shaft 30 is a circular actuating grip 34. The hollow shaft 30 or the drive shaft 20 has a circumferential gearing 36 into which a spring loaded arresting means 38 engages in order to secure in releasable fashion the set radial position of the cutting blade 6.

Axially adjoining the hollow shaft 30 is a rotation coupling 26 seated on the drive shaft 20, that passes over, at a first stub 27, into a first ring channel 28 that opens out in ring channel 23 between the hollow shafts. The channel 23 passes over into an inflow channel 12 in the cutter holder 2, said channel opening out at the free end of the cutter holder. The rotation coupling 26 passes over from a second stub 29 into a second ring channel 29a that opens out in the central channel 25 of the inner hollow shaft 22. Channel 25 passes over into a central outflow channel 14 in the cutter holder 2 that likewise exists at the free end of the cutter holder 2. From a reservoir, via channels 27, 28, 23, 12, rinsing solution can be fed to the cutting location and again be led off together with cuttings via channels 14, 25, 29a.

Capable of being attached, via a chuck jaw 40, on the end of the drive shaft 20 lying opposite to the cutter holder 2, is an actuating crank 48 (represented only partially), with a split inner jaw 42 being drawn down over the drive shaft 20 by means of a cap nut 44. The pinion 8, the hollow shaft 30, possibly the hollow shafts 22 and 24 of the drive shaft, as well as the rotation coupling 26 can be coverably and releasably joined with one another, in this case, the chuck jaw 40 then serves for establishing the axial positions of the individual parts. The plug-on connection of the individual parts permits the cutting tool to be easily disassembled, cleaned and again reassembled.

I claim:

1. Device for cutting a thread in a cup-shaped bone, in particular in the acetabulum of a human pelvis bone, comprising a cutter holder on a drive shaft with a radially, outwardly directed cutting blade on the cutter holder, a cutter gauge capable of being fixed in the socket space, said cutter gauge provided with a central boring and an open, helical cutting channel running spirally about the longitudinal axis of the boring, wherein the cutter holder is capable of being introduced centrally into the boring of the cutter gauge and is capable of being set into a forcefully guided helical cutting movement with the introduction of the cutting blade into the cutting channel.

2. Device according to claim 1, wherein the cutting blade is affixed in radially displaceable fashion in the cutter holder.

3. Device according to claim 1, wherein the cutter holder has a cylindrical form fitting into the boring of the cutter gauge and, running about the axis of the drive shaft, an external thread that is capable of being screwed in the cutting channel at the time of, or after, introduction of the cutting blad into the cutting channel.

4. Device according to claim 1, wherein the cutter gauge has a hemispherical outer form conformed to the hollow cup space.

5. Device according to claim 1, wherein the cutter holder is structured hemispherically at its free end.

6. Device according to claim 1, wherein the cutting blade is disposed at the hemispherical end of the cutter holder.

7. Device according to claim 1, wherein the cutting blade is affixed in a radially displaceable fashion in a radial groove in the cutter holder.

8. Device according to claim 1, wherein the cutting blade has, in the radial direction, a gearing (18) that works together with a setting pinion affixed in the cutter holder and is adjustable by means of an adjusting element.

9. Device according to claim 8, wherein the setting pinion is affixed parallel to the axis of the drive shaft and that the adjusting element is a hollow shaft (32), disposed about the drive shaft, with an actuating grip, and with an external gearing cooperating with the setting pinon.

10. Device according to claim 9, wherein there is provided between the adjusting element (30) and the drive shaft an arresting means for the releasable fixing of the radial position of the cutting blade (6).

11. Device according to claim 1, when the cutter gauge has a fixing pin (56) directed outwardly against the bone.

12. Device according to claim 1, wherein the cutter gauge contains at least one stop for limiting the cutting movement of the cutting blade in the cutting channel.

13. Device according to claim 1, including means for feeding and leading away a rinsing solution at the cutting location.

14. Device according to claim 13, wherein the means for feeding and leading away the rinsing solution includes inflow channel and outflow channels running inside the drive shaft and inside the cutter holder, and an inlet and outlet feed coupling on the drive shaft.

15. Device according to claim 1, including an actuating crank capable of being attached to the end of the drive shaft lying opposite to the cutter holder.

16. Device according to claim 15, wherein the actuating crank can be attached to the drive shaft by means of a chuck jaw.

17. Device according to claim 1, wherein the hollow shaft as well the feed coupling for the rinsing solution, and the pinion, are capable of being plugged onto the cutter holder and the drive shaft and fixed in their axial position by means of the chuck jaw.

18. Device according to claim 1, including attaching means on the cutter gauge for installing hand grips.

* * * * *

UNITED STATES PATENT AND TRADEMARK OFFICE
CERTIFICATE OF CORRECTION

PATENT NO. : 4,856,503

DATED : August 15, 1989

INVENTOR(S) : Klaus-Dieter Schelhas

It is certified that error appears in the above-identified patent and that said Letters Patent is hereby corrected as shown below:

Column 1, line 63
    "sprial" should be -- spiral--

Column 6, line 1
    "blad" should be --blade--

Column 6, line 24
    "pinon" should be --pinion--

Signed and Sealed this

Seventh Day of August, 1990

Attest:

HARRY F. MANBECK, JR.

*Attesting Officer*  *Commissioner of Patents and Trademarks*